United States Patent
Porter et al.

(10) Patent No.: US 7,726,175 B2
(45) Date of Patent: *Jun. 1, 2010

(54) EMBEDDED PIEZOELECTRIC MICROCANTILEVER SENSORS

(75) Inventors: Timothy L. Porter, Flagstaff, AZ (US); Michael P. Eastman, McAllen, TX (US)

(73) Assignee: Arizona Board of Regents, A Body Corporate of the State of Arizona, acting for Northern Arizona University, Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/137,231

(22) Filed: Jun. 11, 2008

(65) Prior Publication Data

US 2009/0090168 A1    Apr. 9, 2009

Related U.S. Application Data

(63) Continuation of application No. 11/657,250, filed on Jan. 24, 2007, now Pat. No. 7,395,693, which is a continuation of application No. 11/004,555, filed on Dec. 2, 2004, now Pat. No. 7,168,294, which is a continuation of application No. 10/454,346, filed on Jun. 3, 2003, now Pat. No. 6,854,317.

(60) Provisional application No. 60/385,664, filed on Jun. 3, 2002.

(51) Int. Cl.
*G01N 7/04* (2006.01)
*G01N 7/00* (2006.01)

(52) U.S. Cl. .................. 73/23.2; 73/31.05; 73/29.05

(58) Field of Classification Search .................. 73/23.2, 73/24.06, 29.05, 31.01, 31.05

See application file for complete search history.

(56) References Cited

U.S. PATENT DOCUMENTS 3,260,104 A    7/1966    King, Jr.

(Continued)

FOREIGN PATENT DOCUMENTS

JP    2000-214072 A    8/2000

(Continued)

OTHER PUBLICATIONS

"Integral"—Oxford English Dictionary, Second Edition. 1989. Accessed online on Jun. 20, 2009. <http://dictionary.oed.com>.*

(Continued)

*Primary Examiner*—Lisa M Caputo
*Assistant Examiner*—Punam Patel
(74) *Attorney, Agent, or Firm*—McDonnell Boehnen Hulbert & Berghoff LLP

(57) ABSTRACT

An apparatus and method for sensing chemical and/or biological analytes includes a deflectable arm of a microcantilever at least partially embedded within a sensing element. A gaseous or liquid medium which may include the analyte being detected is introduced to the sensing element. The sensing element undergoes volumetric expansion or contraction in the presence of the analyte sought to be detected, typically by adsorbing the analyte. The volumetric change of the sensing element causes the deflectable arm to deflect. The deflectable arm includes at least one measurable physical property which changes when the arm deflects. Detecting means are provided to measure the change in the physical property to determine the presence and amount of analyte present. An array of microcantilevers in which each microcantilever is dedicated to detecting a particular analyte which may be included in the medium, is also provided.

12 Claims, 6 Drawing Sheets

U.S. PATENT DOCUMENTS

| | | | |
|---|---|---|---|
| 4,361,026 | A | 11/1982 | Muller et al. |
| 4,708,019 | A | 11/1987 | Rubner et al. |
| 5,445,008 | A | 8/1995 | Wachter et al. |
| 5,461,274 | A | 10/1995 | Yuji et al. |
| 5,483,822 | A | 1/1996 | Albrecht et al. |
| 5,536,963 | A | 7/1996 | Polla |
| 5,698,931 | A * | 12/1997 | Shibata et al. ............ 310/338 |
| 5,719,324 | A | 2/1998 | Thundat et al. |
| 5,877,411 | A | 3/1999 | Namerikawa et al. |
| 5,955,659 | A | 9/1999 | Gupta et al. |
| 6,016,686 | A | 1/2000 | Thundat |
| 6,041,642 | A | 3/2000 | Duncan |
| 6,109,852 | A | 8/2000 | Shahinpoor et al. |
| 6,183,097 | B1 | 2/2001 | Saif et al. |
| 6,196,052 | B1 | 3/2001 | May et al. |
| 6,201,980 | B1 | 3/2001 | Darrow et al. |
| 6,287,765 | B1 | 9/2001 | Cubicciotti |
| 6,289,717 | B1 | 9/2001 | Thundat et al. |
| 6,447,887 | B1 | 9/2002 | Claus et al. |
| 6,475,750 | B1 | 11/2002 | Han et al. |
| 6,514,689 | B2 | 2/2003 | Han et al. |
| 6,523,392 | B2 | 2/2003 | Porter et al. |
| 2003/0137216 | A1 | 7/2003 | Tamayo de Miguel et al. |

FOREIGN PATENT DOCUMENTS

| | | |
|---|---|---|
| WO | WO 01/81857 | 11/2001 |

OTHER PUBLICATIONS

Hughes, et al., (2001), "Characteristics and mechanisms in ion-conducting polymer films as chemical sensors polyethyleneoxide", Journal of the Electrochemical Society Electrochem. Soc USA, vol. 148, No. 4, pp. H37-H44.

Porter, et al., (2001), "Sensor based on piezoresistive microcantilever technology", Sensors and Actuators A, Elsevier Soequoia S.A., Lausanne, Ch, vol. 88, No. 1, pp. 47-51. Jan. 2001.

Amrani, et al., (1995), "High-frequency measurements of conducting polymers: development of a new technique for sensing volatile chemicals", Measurement Science and Technology, IOP, Bristol, GB, vol. 6, No. 10, pp. 1500-1507.

Baselt et al., "Biosensor Based on Force Microscope Technology," J. Vac. Sci. Technol., 1996, vol. 14(2), pp. 789-793.

Eastman et al., "Application of the Solubility Parameter Concept to the Design of Chemiresistor Arrays," Journal of the Electrochemical Society, 1999, vol. 146, pp. 3907-3913.

Fritz et al., "Translating Bio Molecular Recognition Into Nanomechanics," Science, Apr. 14, 2000, vol. 14, 288, pp. 316-318.

Lonergan et al., "Array-Based Vapor Sensing Using Chemically Sensitive, Carbon Block-Polymer Resistors," Chem. Mater., 1996, vol. 8, pp. 2298-2312.

Lundberg et al., "Resistivity of a Composite Conducting Polymer as a Function of Temperature, Pressure, and Environment: Applications as a Pressure and Gas Concentration Transducer," J. Appl. Phys., 1986, vol. 60, pp. 1074-1079.

Porter et al., "Polymer-Based Materials to be Used as the Active Element in Microsensors: A Scanning Force Microscopy Study," Journal of Scanning, 2000, vol. 22, pp. 1-5.

Porter et al., "Sensor Based on Piezoresistive Microcantilever Technology," Sensors and Actuators, 2001, vol. A88, pp. 47-51.

Ricco et al., "Chapter 23: Chemically Sensitive Interfaces on Surface Acoustic Wave Devices," *Interfacial Design and Chemical Sensing*, Washington D.C., 1994, pp. 264-279.

Ruschau et al., "0-3 Ceramic/Polymer Composite Chemical Sensors," Sensors and Actuators, 1989, vol. 20, pp. 269-275.

Talik et al., "Sensing Properties of the CB-PCV Composites for Chlorinated Hydrocarbon Vapours," J. Mater. Sci., 1992, vol. 27, pp. 6807-6810.

Thayson et al., "Polymer-Based Stress Sensor with Integrated Readout", Journal of Physics D: Applied Physics, 2002, vol. 35(21), pp. 2698-2703.

Thundat et al., "Thermal and Ambient-Induced Deflections of Scanning Force Microscope Cantilevers," J. Appl. Phys. Lett., 1994, vol. 64(21), pp. 2894-2896.

Wachter et al., "Microchemical Sensors for Chemical and Physical Measurements," Rev. Sci. Instrum., 1995, vol. 66(6), pp. 3662-3667.

Machine-assisted English language translation from JPO website of JP-2000214072-A.

* cited by examiner

FIG. 4

PEO+AB (virus) - PEO+AB (water) (scaled to PEO)

Resistance Change (Ohms) vs. Time (s)

EMBEDDED PIEZOELECTRIC MICROCANTILEVER SENSORS

CROSS-REFERENCE TO RELATED APPLICATION

This application claims priority of U.S. patent application Ser. No. 11/657,250, filed Jan. 24, 2007, which claims priority to Ser. No. 11/004,555 filed Dec. 2, 2004, now U.S. Pat. No. 7,168,294 which claims priority of U.S. patent application Ser. No. 10/454,346, filed Jun. 3, 2003, now U.S. Pat. No. 6,854,317 which claims priority to U.S. Provisional Patent Application No. 60/385,664, filed Jun. 3, 2002, all of which are hereby incorporated by reference in their entirety.

FIELD OF THE INVENTION

The present invention relates most generally to microsensors for sensing chemical or biological analytes, and, more particularly, the present invention is related to embedded deflectable microcantilever sensors used to sense the presence of chemical and/or biological analytes.

BACKGROUND OF THE INVENTION

The construction of rugged, inexpensive, reliable and small chemical microsensors whose output can be expressed in terms of a measurable electrical signal such as DC conductivity is of current interest. The goal of current research and development is to construct devices that can detect and identify chemical or biological analytes alone or in a complex mixture. Ideally, such sensors should be able to function in either a liquid or vapor environment.

Among the systems receiving attention in this regard are carbon-black organic polymer composites which are deposited by spin or drop coating on interdigitated arrays. Inclusion of the carbon black component into the active sensor material is for the sole purpose of obtaining a measurable DC conductivity through the non-conductive active polymer material. The introduction of analyte material causes polymer swelling and consequent resistance changes of the polymer composite films. To identify specific vapors from a suite of possible substances and to determine the concentration of that vapor or to carry out similar measurements on multi-component systems requires the construction of arrays of sensing elements. Pattern recognition techniques or principal component analysis of the output of an array of sensors can be used for purposes of analyte identification and quantification.

A number of shortcomings are associated with the use of the carbon-black organic polymer composites. First, it is difficult to reliably reproduce the performance characteristics of a given set of chemiresistor elements due to uncontrollable variations in composite construction. Second, spin coated or drop coated carbon-black polymer composites are inherently metastable in nature and may change or degrade with time. Third, metastable composite systems may not reliably adhere to a substrate surface. Fourth, repeated exposure of the metastable sensor element to analyte vapor may lead to misleading drifts and/or changes in performance characteristics. Fifth, the carbon in a composite material may slowly release analyte material following exposure to analyte and thus have a slow recovery time. Sixth, the interdigitated arrays generally consist of two components—a glass substrate and a metallic thin film or wire along with interface regions. Such complicated structures can lead to adhesion problems. Furthermore, carbon-black cannot be used for biological sensing because sensors based on biological molecules and attached to a substrate cannot effectively incorporate a material such as carbon-black.

Another approach for sensing analytes includes the use of vibrating microcantilever structures. Using this technique, a microcantilever is driven into oscillation at one of its resonant frequencies using external circuitry. The microcantilever itself is coated with an active sensing material. Absorption of analyte molecules on the vibrating cantilever changes the frequency or amplitude of the oscillation and this change is sensed by the electronic circuitry.

There are, however, several shortcomings associated with the use of vibrating or oscillating microcantilevers. The sensing materials coated on the microcantilevers can easily delaminate during use. Sensors based on this technology require extensive electronic circuitry, both to drive the microcantilevers into oscillation and to sense the change in microcantilever frequency and/or amplitude upon exposure to analyte. Additionally, fabricating arrays consisting of many, close packed vibrating cantilevers is extremely difficult due to differences in cantilever resonant frequencies and the proximity of the cantilevers to one another. Another limitation of prior art cantilevers is that their construction results in an overly fragile device leading to a high probability for breakage during assembly and/or use. Finally, these vibrating or oscillating microcantilever sensing devices are highly subject to external vibration or movement, making fabrication of truly portable devices difficult.

To overcome the mechanical disadvantages of the vibrating microcantilever sensors a new microsensor which uses a microcantilever and a sensing element formed beneath the microcantilever and in contact with the microcantilever have been developed. In this type of sensor, the sensing material is chosen so that in the presence of the desired analyte material, the sensing element undergoes a volumetric expansion or contraction including in the vertical direction. Such a volumetric change causes the upward or downward deflection of the initially stationary microcantilever. The microcantilever need not be driven onto oscillation so the associated extensive electronic circuitry is not required. However, these sensors still require a delicate mechanical connection between the sensing material and the microcantilever, which can cause breakdowns, such as tip lift-off in rugged environments.

Accordingly, a need exists for an improved microsensor that is not dependent on sensitive electronics or mechanical connections to operate.

BACKGROUND OF THE INVENTION

The present invention provides a method and apparatus for determining the presence and quantity of biological and/or chemical analytes using a deflectable arm of a microcantilever that is at least partially embedded within a sensing material formed on a surface. The sensing material is chosen to undergo a volumetric expansion or contraction in response to the presence of an analyte or analytes desired to be detected. A volumetric change, with a component in a vertical direction of the sensing material causes the embedded portion of the arm to move vertically and places a measurable strain on the arm. The microcantilever arm includes at least one measurable physical property which changes when stress is applies to the arm. This change is measured to determine the presence and quantity of the analyte or analytes of interest.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following ures:

FIG. 4 is a graphical depiction of the response properties of an exemplary embodiment of an embedded microcantilever sensor according to the present invention;

DETAILED DESCRIPTION OF THE INVENTION

The present invention provides a method and apparatus for detecting the presence and quantity of an analyte in a gaseous or liquid medium by introducing the medium to a sensing material formed on a surface. At least partially embedded within the sensing element is an arm of a microcantilever. In the presence of the analyte sought to be detected, the sensing material undergoes a volumetric expansion or contraction including in the vertical direction. Such expansion or contraction causes the embedded portion of the arm to move vertically and places a measurable strain on the arm.

The sensing material may be a chemical sensor material such as a polymer or a biological sensor material such as a biomolecule, biofilm, or a composite of these materials. The sensing material may be formed in a discrete portion on a portion of the deflectable arm, such as on the tip end of the cantilever, or as a continuous coating of the sensing element may be formed over the surface such that a portion of the deflectable arm is embedded therein.

The microcantilever itself is formed on a substrate separate from the surface including the sensing material. Conventional semiconductor processing technology may be used to form the embedded microcantilever. Various configurations and orientations of the microcantilever may be used. The microcantilever includes an overhang portion which extends over the edge of the microcantilever substrate and allows for the substrate and the surface containing the sensing material to be positioned in close proximity to one another such that the deflectable arm of the embedded microcantilever may be at least partially embedded within the sensing material. A micromanipulator may be used to position and align the components.

The deflectable arm of the microcantilever will preferably be formed of semiconductor materials resistant to attack by analytes and the gaseous and liquid media which are introduced to the arrangement and which may include the targeted analyte. The deflectable arm is usable in both gaseous and liquid environments. The deflectable arm of the microcantilever includes at least one measurable physical property which changes when stress is created in the deflectable arm by the deflection of the embedded portion of the deflectable arm responsive to the volumetric change of the surrounding sensing material.

The present invention also provides detecting means such as various electric circuits which detect the change in the measurable physical property or properties of the deflectable arm. The measurable physical property will preferably be measured prior to and after the introduction of the medium which may include the analyte sought to be detected. The medium is introduced to intimately contact the sensing material.

Figure 1:
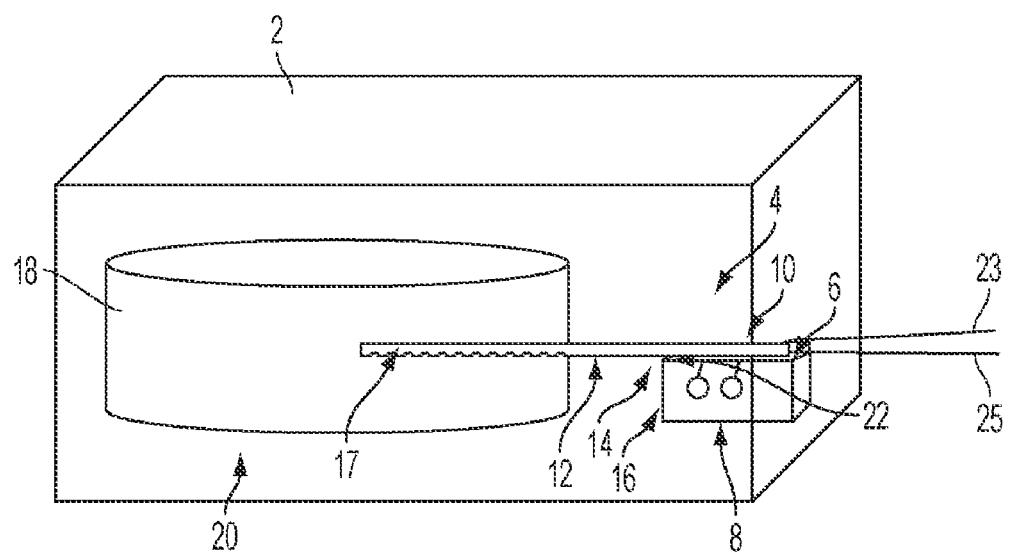
FIG. 1 is a perspective view of an exemplary embodiment of an embedded microcantilever sensor according to the present invention.

Now turning to the figures, FIG. 1 shows an exemplary embodiment of an embedded microcantilever structure. Generally, the microcantilever 2 includes a deflectable arm 4 and base 6 formed over a substrate 8. The substrate 8 may be a conventional semiconductor substrate such as silicon, gallium arsenide, or other suitable materials chosen to be deflectable yet resilient. The microcantilever 2 including the deflectable arm 4 may be formed using conventional semiconductor processing techniques and the bulk of deflectable arm 4, may preferably be formed of silicon nitride, silicon, or other suitable materials. One end of deflectable arm 4 is formed integral with substrate 8. In the exemplary embodiment, one end of deflectable arm 4, the anchor portion 10 is fixedly coupled to substrate 8 through the base 6, while the opposite end of deflectable arm 4, the overhang portion 12, is free to move in the vertical direction.

The dimensions of microcantilever 2 including the deflectable arm 4 will vary according to various embodiments. In one exemplary embodiment, the length of the deflectable arm 4 may range from 100 microns to 200 microns, the height may range from 10 microns to 50 microns, and the width may range from 25 microns to 75 microns but other dimensions may be used alternatively. Furthermore, it should be noted that the essentially horizontal configuration of deflectable arm 4 in its illustrated rest position is exemplary only and that deflectable arm 4 may be formed tilted downward with respect to the horizontal when in its rest position. In that case, the axis of deflectable arm 4 may form an acute angle with each of top and bottom of the substrate 8.

The deflectable arm 4 and the microcantilever 2 are preferably formed over substrate 8 so as to include the overhang portion 12 disposed over a substrate 8 upon formation. After the formation of the microcantilever 2, the substrate 8 is diced or fragmented to produce an edge 14 which the overhang portion 12 extends beyond. It should be understood that the edge 14 of the substrate 8 and the vertical wall 16 of the base 6 are not limited to being coplanar as in the illustrated exemplary embodiment. The critical consideration is that the deflectable arm 4 includes an overhang portion 12 which extends past the edge 14 of substrate 8 so as to enable the deflectable arm 4 to be embedded 17 within a sensing element 18 formed on a further substrate surface 20.

FIG. 1 shows an exemplary embodiment of deflectable arm 4 where the overhang portion 12 of the arm 4 is at least partially embedded within the sensing material 18 formed on the surface of the further substrate 20. The further substrate surface 20 may be a ceramic or semiconductor substrate, but other materials may be used in other exemplary embodiments. Because the overhang portion 12 of the deflectable arm 4 extends beyond the edge 14 of the substrate 8, the components may be positioned such that overhang portion 12 of the deflectable arm 4 is at least partially embedded with the sensing material 18, as shown. In the embodiment shown, about one-third of the overhang portion 12 of the deflectable arm 4 is embedded within the sensing material 18. However, this is intended to be exemplary only and the deflectable arm and the portion of the deflectable arm embedded within the sensing material may take on other configurations.

The materials of construction of the deflectable arm 4 should be chosen such that the deflectable arm bends responsive to a volumetric change of the sensing material 18 in the vertical direction, even if the deflectable arm 4 is submerged within a liquid medium such as may be introduced to the sensing material 18 for analysis. For example, the cantilever may be constructed of a photoresist material, such as "SU-8" using gold or other material as the resistive element. A discussion of such materials is provided in the publication to Thaysen et. al., http://www.mic.dtu.dk/research/mems/publications/Papers/thaysen%20mems%202002.pdf), the disclosure of which is incorporated herein by reference.

The deflectable arm 4 further includes at least one measurable physical property which changes when a stress is placed on the arm by the deflection of the embedded portion, such as in response to a vertical volumetric expansion of the surrounding sensing material as will be shown in figures. An example of a measurable physical property which changes when the embedded portion of the deflectable arm 4 deflects is resistance. To provide a resistance which changes when the embedded portion of the deflectable arm 4 deflects, a piezoresistive member 22 is formed within the deflectable arm 4. According to other exemplary embodiments, the piezoresistive member may be formed on the top surface or the underside of the deflectable arm.

According to an exemplary embodiment, the piezoresistive member 22 may be a film such as barium titanate formed integrally within the deflectable arm 4 during the microcantilever fabrication process. When the deflectable arm 4 bends, the resistance of the piezoresistive member 22 changes due to the mechanical stress in the member. The non-stressed resistance of the microcantilevers may be on the order of 2 k ohms according to an exemplary embodiment. This exemplary measurable physical property therefore changes due to bending. Detecting means are used to measure this change in resistance. The microcantilever sensitivity and the detecting means precision is such that bending of only a few tens of angstroms will result in a measurable resistance change.

To measure the change in resistance according to one exemplary embodiment, conductive wires, such as wires 23, 25 in FIG. 1, may be coupled to the piezoresistive member through contacts. In such an embodiment, each of the contacts would extend through the top surface of the deflectable arm to contact the piezoresistive member. The conductive wires can then be coupled to a conventional electric circuit capable of measuring the resistance of piezoresistive member.

It should be understood that resistance as the measurable physical property of piezoresistivity is intended to be exemplary only. According to other exemplary embodiments, various other physical properties which change when the deflectable arm bends may also be used in conjunction with associated detecting means capable of measuring this change. For example, the deflectable arm may be designed such that it's optical transmittance or refractive index varies in response to deflection. This is particularly advantageous when it is desired to integrate the sensor into a photonic device. In a preferred embodiment, the detecting means is capable of measuring the extent of deflection. An electric circuit or other means may in turn be provided to facilitate measurement of the change in the measurable physical property. When measuring the change, the measurable physical property is preferably measured prior to and after bending, and the results compared to detect a change and the degree of change. The change itself can then be associated with the presence of the analyte sought to be detected, and the degree of change in the physical property will preferably correspond to the degree of arm deflection which, in turn, will preferably correspond to the amount or concentration of the analyte present. According to another exemplary embodiment, the deflectable arm may include more than one measurable physical property which changes when the arm deflects.

The sensing material 18 may be formed on the surface 20 using conventional methods. For the illustrated exemplary embodiment in which the sensing material 18 is formed as a discrete pad of material formed on the surface 20 and partially encasing the overhang portion 12 of the deflectable arm 4, the sensing material may be formed by drop deposition, such as by using microcapillaries, dipping of the cantilever into a material solution, or using ink jet printer technologies to form a droplet directly atop the overhang portion of the deflectable arm. Other methods for depositing the sensing material 18 may be used alternatively. Sensing material deposits may take on the shape of a puddle, pad or droplet. Alternatively, the surface 20 or a portion of the deflectable arm 4 itself may be derivatized prior to deposition of the sensing material, to promote adhesion.

The dimensions of sensing material deposit are chosen in conjunction with the dimensions of deflectable arm 4. The lateral size of the sensing material deposit may be as small as a few microns. The lateral size and length of the sensing material deposit along the length of the deflectable arm are chosen to ensure a sufficiently large portion of the deflectable arm is embedded. According to another exemplary embodiment, the sensing material may be formed over the entirety of surface of the substrate. In such am embodiment conventional coating or other methods may be used, however, discrete deposits of sensing material are preferable when an array of microcantilevers will be used.

The sensing material may be sensitive to chemicals or biological materials. For the case of a chemical sensing material, pure polymers or composite materials of combination of polymers can be used to detect either liquid or vapor phase analytes. After formation, polymeric sensing materials include a somewhat rubbery consistency in an exemplary embodiment. The polymeric chemical sensing material is chosen to undergo volumetric expansion or contraction in the presence of at least one analyte sought to be detected. This occurs as the analyte is attracted to and combines with the sensing material, typically by partitioning into the polymer volume, or by adsorption. Exemplary polymeric chemical sensor materials include: Polyvinyl compounds including polyvinylchloride; polyvinylidene chloride or fluoride and their co-polymers; polyvinyl acetate (PVA) and co-polymers of polyvinyl acetate, polymethyl vinyl ether; polyvinyl alcohol and it's copolymers with ethylene and vinyl acetate; polystyrene, polyalphamethylstyrene and related polymer and co-polymers; poly(4-vinylphenol), poly(styrene-co-allyl alcohol), poly(methylstyrene). A particular group of vinyl polymers of interest are ion exchange polymers comprised of, for example, polystyrene resins with ionic groups including sulfonate, carboxylate, amino, ammonium, phosphate, acetylacetonate, and other ionic exchange and ion selective resins known in the art including crown ethers and related ligand polymers.

Polyolefins and polyalphaolefins, including polyethylene polypropylene, polyisobutylene, polymethyl pentene, polybutadines, ethylene propylene co-polymers, ethylene alpha olefin co-polymers, cyclic olefin co-polymers for example materials sold under the trade name of Topas™ by Ticona.

Elastomers including styrene co-polymers (SBS, SIS, SBR) and thermoplastic olefin elastomers (generally referred to as TPO), butadiene nitrile co-polymers and elastomers comprised of polyurethanes (TPU) and co-polyesters (COPE), as well as polyether polyamide resins (PEBA), for example Pebax™ resins sold by Atofina and silicone rubbers and elastomers.

Acrylic polymers including polyalkyl (meth)acrylates such as polymethyl (meth)acrylate, polybutyl (meth)acrylate, polyphenoxy ethyl (methacrylate), poly(meth)acrylic acid, poly(meth)acrylamide, polyalkyl (methacrylamides) and the wider range of polymers generally referred to as acrylics.

Polyethers including poly methylene oxide, poly ethylene oxide, polypropylene oxide, co-polymers of ethylene oxide and propylene oxide, poly tetrahydrofuran, and the related polythioethers as well as polyphenylene oxide and it's co-polymers.

Polyamides including nylon 6, nylon 66, nylon 6 66, nylon 11, nylon 12, and the various aliphatic nylon copolymers and amorphous nylons including, by example, materials under the Trade Name of Grilamide™ sold by EMS and similar materials containing both aliphatic and aromatic moieties.

Polycarbonates, polysulfones, polyureas, polyurethanes, polyesters such as PET and PETG, and naturally derived polymers such as cellulosics and modified cellulosic including methylcellulose, ethylcellulose, dextran, and starch based polymers.

A particularly preferred group of potential polymers include: poly(vinyl acetate) (PVA), poly(isobutylene) (PIB), poly(ethylene vinyl acetate) (PEVA), poly(4-vinylphenol), poly(styrene-co-allyl alcohol), poly(methylstyrene), poly(N-vinylpyrrolidone), poly(styrene), poly(sulfone), poly(methyl methacrylate), and poly(ethylene oxide) (PEO).

According to another exemplary embodiment, the polymeric chemical sensing material may be a composite material including more than one of the above or other exemplary compounds. For example, a blend of styrene and polymethylmethacrylate, or a "composite" material prepared by dispersing particles of PEO in polydimethyl siloxane.

Other sensing materials may be used alternatively. Upon exposure to the targeted analyte, the chemical sensor undergoes a volumetric change including in a vertical direction to place a stress on the embedded deflectable arm in a vertical direction when the analyte is adsorbed by the sensing material.

The sensing material may also be a biological sensor such as a biomolecule, which undergoes a conformational change in the presence of the analyte sought to be detected. According to one exemplary embodiment, the sensing material may be a thiolated single strand DNA (deoxyribonucleic acid) embedded within a matrix material containing particles of gold. In such an embodiment the thiolated end of the DNA single strand adheres well to gold. Such a biological sensor can be used to detect the complementary DNA strand. DNA preferably exists in a double strand configuration. If the complementary DNA strand (the analyte) is included within the medium introduced to the sensing element, the complementary strand would strongly bind to the thiolated strand effectively changing the thickness of the DNA layer in the matrix material or, stated alternatively, produce a volumetric increase or decrease in the vertical direction. In another alternative embodiment of a DNA sensing device a amino terminated DNA strand could be used in a polymer prepared of butyl acrylate co-maleic anhydride, 95:5 w/w using ethyl acetate as the polymerization solvent and di-benzyl peroxide (0.05%) as the initiator. In such an embodiment, after polymerization the resultant polymer would be allowed to react with the amine terminated single strand DNA resulting in a sensing material that would increase in volume when exposed to a complimentary DNA strand.

According to another exemplary embodiment of a biological sensor, a volume of antibodies, specific to the desired analyte to be sensed such as a particular virus, is embedded within a polymeric material. When the analyte virus is present, it is strongly attracted to and subsequently binds to the antibodies within the polymer. In this manner, the thickness increases and represents a volumetric change in the vertical direction. According to other exemplary embodiments, other biological sensing elements may be used which undergo a physical or morphological change in response to the presence of the analyte sought to be sensed, including composite materials consisting of a host material in which biological molecules are included. In each case, the sensing material adsorbs the analyte and expands or contracts volumetrically in the vertical direction deflecting the embedded portion of the deflectable arm and creating a measurable stress on the portion of the deflectable arm attached to the base. According to yet another exemplary embodiment, the biological sensor may be chosen to volumetrically contract in the vertical direction in response to the presence of the analyte sought to be detected.

According to various exemplary embodiments, sensing material may also expand in the lateral direction in addition to in the vertical direction. In such an embodiment the lateral expansion of the sensing material may also contribute to the vertical expansion of the material. The size of such a lateral expansion would depend on the analyte/sensing material chosen and the construction of the substrate upon which the sensing material was placed.

Although the schematic diagram in FIG. 1 shows one exemplary embodiment of the embedded microcantilever other exemplary embodiments of the embedded microcantilever are within the scope of the current application.

For example, although the deflectable arm 4 is parallel to the substrate surface 20 in the embodiment shown in FIG. 1, it should be understood that the arm may also be angled downward in its rest position. Stated alternatively, the angle which the deflectable arm 4 makes with the horizontal in its rest position may be an acute angle. Similar to the other exemplary embodiments, the deflectable arm would have one end attached to the base and one end would be at least partially embedded within the sensing material.

Figure 2A:
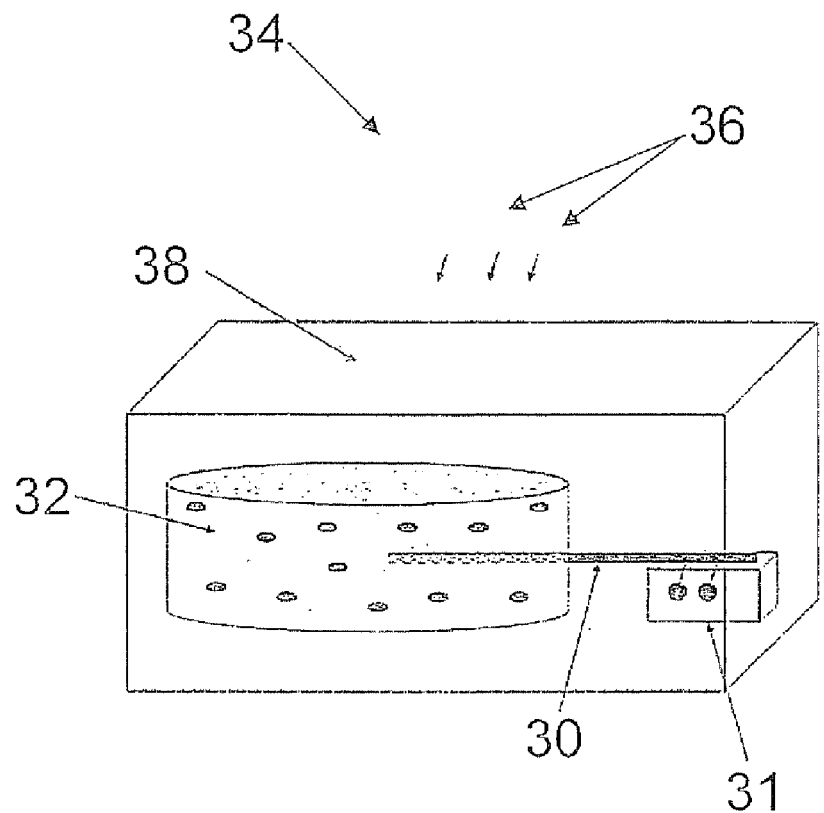
FIGS. 2*a* and 2*b* are perspective views of the operation of an exemplary embodiment of an embedded microcantilever sensor according to the present invention.
Figure 2B:
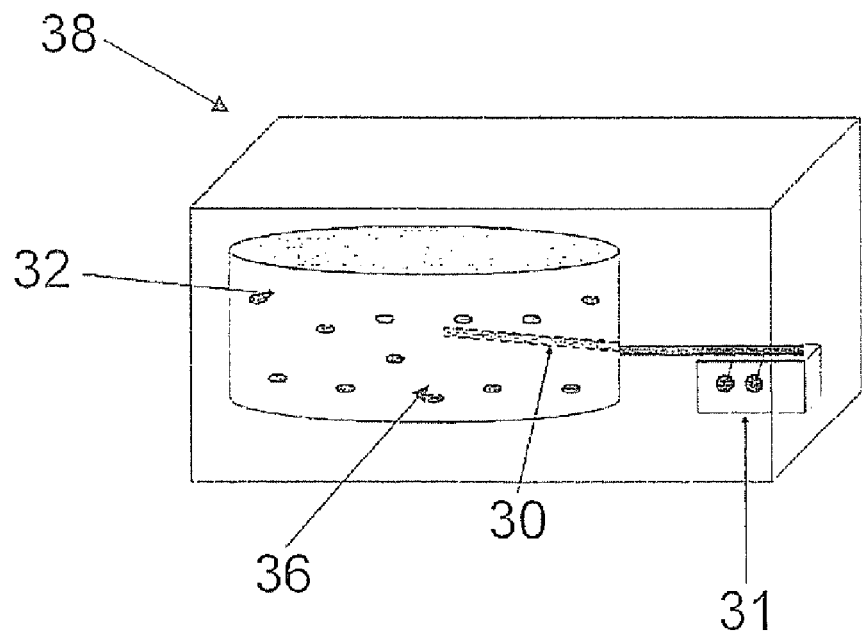

During a typical operation, as shown schematically in FIGS. 2a and 2b, the deflectable arm 30 on the microcantilever sensor 31 is rigid and fixed into position and at least partially embedded within the sensing material 32 in a rest position, as shown in FIG. 2a. Then the medium 34 being analyzed for the targeted analyte 36 is introduced to the arrangement 38 such that the medium intimately contacts the sensing material 32. If the analyte 36 is present in the medium 34, the sensing material 32 undergoes a volumetric expansion in the vertical direction causing upward or downward displacement of the embedded portion of the deflectable arm 30, as shown in FIG. 2b. The degree of displacement will vary with the volumetric change of the sensing material in the vertical direction and also preferably with the concentration or amount of detected analyte.

It should be noted that preferably the deflectable arm 30 is a resilient member that can be reused after deflecting to detect an analyte. After use in detection, as shown in FIG. 2b, the resilient deflectable arm 30 in such an embodiment would return to the rest position pictured in FIG. 2a.

Now referring to FIG. 2a, the deflectable arm 30 of the microcantilever is shown to be configured substantially horizontal when in rest position. Exemplary displaced position (shown by dashed lines in FIG. 2b) shows the embedded portion of the deflectable arm 30 bent or displaced upward. The extent of vertical displacement or deflection of the embedded portion of the deflectable arm 30 naturally will be proportional to the amount of volumetric expansion in the vertical direction. In turn, according to various exemplary embodiments, the degree of swelling or volumetric expansion in the vertical direction of the sensing element may be proportional to the concentration of the analyte sought to be detected up to a saturation level. According to other exemplary embodiments, this may not be true. Furthermore, according to various exemplary embodiments, the measurable physical property such as resistance of a piezoresistive element may vary linearly with the extent of bending. In other exemplary embodiments this may not be so. Various conventional calibration techniques may be used to correlate the extent of deflection and the associated degree of change of the measurable physical property to the amount or concentration of analyte present.

As above, the sensing material used may be sensitive to a single analyte or to multiple analytes. Furthermore, a composite sensing material may be used to detect any of a number of analytes as indicated by the deflection of the single embedded microcantilever. It is therefore another aspect of the present invention to provide an array of microcantilevers each with an associated sensing element. In this manner, a number of dedicated embedded microcantilevers can be used to detect a particular and distinct analyte. An exemplary array is shown in FIG. 3.

Figure 3:
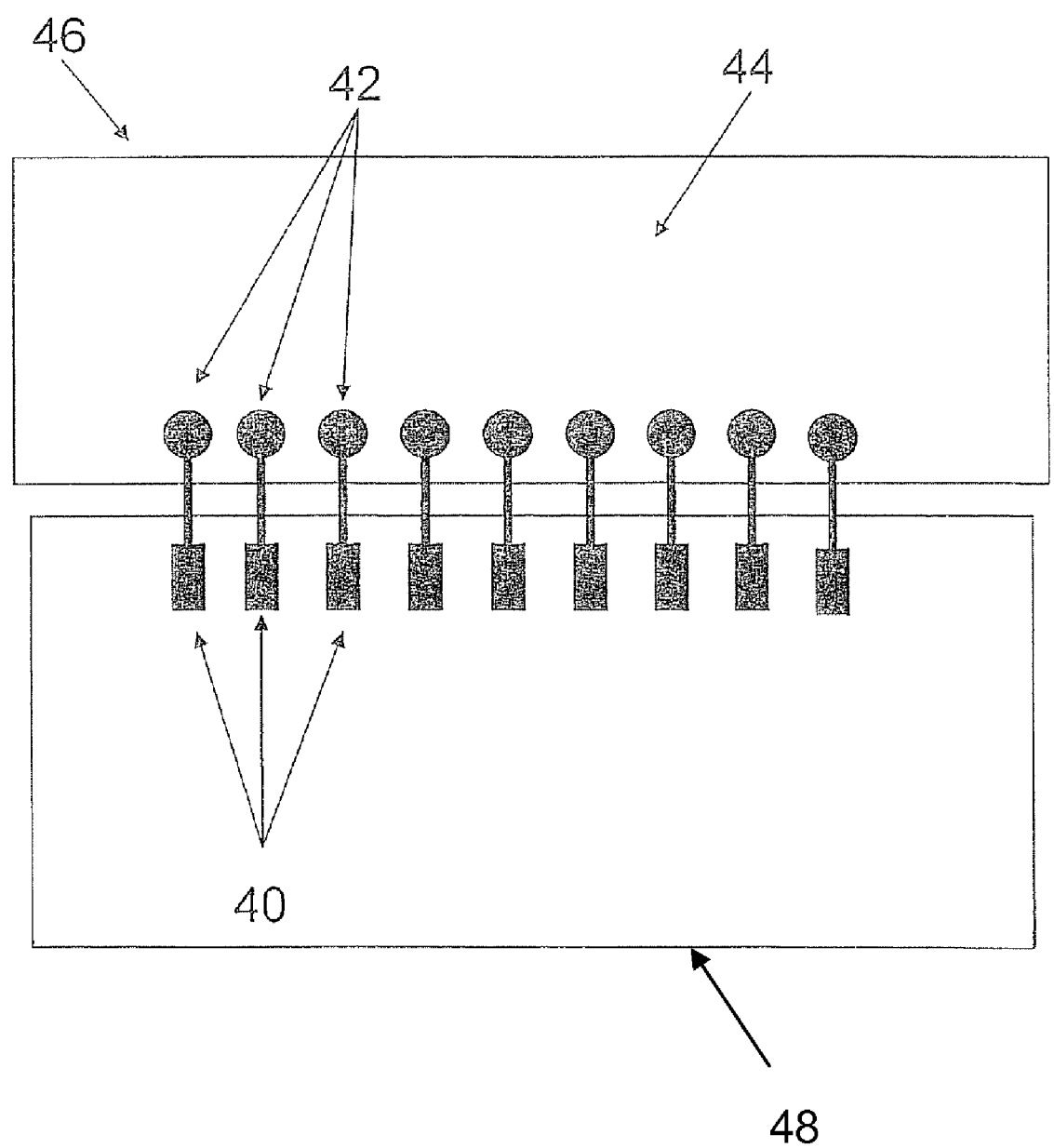
FIG. 3 is a perspective view of an exemplary embodiment of an array of embedded microcantilevers according to the present invention.

Now referring to FIG. 3, an array of nine embedded microcantilevers 40 are shown. Although a linear array of nine embedded microcantilevers formed on common substrate is shown in the exemplary embodiment of FIG. 3, it should be understood that various numbers of embedded microcantilevers may be included and arranged in different configurations according to various other exemplary embodiments. The embedded microcantilevers 40 are as shown and described in conjunction with previous drawings. Discrete deposits of sensing materials 42 are formed on surface 44 of the sensing material substrate 46. The array of sensing material deposits is formed to correspond to the complementary array of deflectable arms on the microcantilevers 40 formed on the microcantilever substrate 48. When the microcantilever substrate 48 and sensing material substrate 46 are positioned in the preferred positions with respect to each other, each deflectable arm is embedded within a discrete deposit of sensing material 42. Each microcantilever is also coupled to detecting means such as an electrical circuit (not shown) capable of measuring a change in at least one physical property of the deflectable arm when the embedded portion bends responsive to a volumetric change in the vertical direction of the sensing material deposit.

Each of the discrete sensing material deposits may be formed of an exemplary chemical or biological sensor such as described above. In the preferred embodiment, each of discrete sensing material deposits may be formed of a different material. In this manner, each dedicated sensing material deposit each sensor may be constructed to have a different level of response to different analytes and undergoing a volumetric change in response to the presence of such analyte. For example, PVA responds strongly to ethyl acetate and weakly for heptane, while poly1,2butadiene responds strongly to heptane and weakly to ethyl acetate. In this manner, a single medium which may contain multiple analytes sought to be detected may be introduced to the arrangement and the presence and amount (or absence) of the various analytes sought to be detected may be independently determined by an embedded microcantilever that each sensor has a different level of response to different analytes. Principal component analysis of the output of an array of sensors can be used for purposes of analyte identification and quantification. In this manner, a medium may be simultaneously analyzed for the presence of multiple analytes.

As is the case with respect to a single embedded microcantilever, the embedded microcantilever array can be calibrated to correlate a measured change in the measurable physical property due to bending to the amount or concentration of the analyte sought to be detected. In the case where the analyte sought to be detected is not present, the embedded microcantilever does not deflect and therefore the measurements taken before and after the introduction of the medium will be substantially the same.

Accordingly to another exemplary embodiment in which an array of microcantilevers is used, the sensing material substrate may be coated with a single coating of a continuous sensing material and multiple microcantilevers may be embedded within the sensing material in order to provide multiple readings and a more accurate determination of the analyte or analytes being detected.

Examples of graphical readings taken from exemplary embodiments of the embedded microcantilevers in accordance with the present invention are provided in FIGS. 4 to 6, below. In the exemplary embedded microcantilever the sensing material, in liquid form, was deposited directly around the tip end of the overhang portion of the deflectable arm of the microcantilever. In this embodiment, approximately ⅓ of the deflectable are length was embedded within the sensing material deposit.

To prepare the detector, a sensing material preparation was first made using a 10:1 polymer powder to solvent ratio, and then the analyte sensitive dopant was added to this liquid polymer mixture at a ratio of 10:1 to form a liquid sensing material. The liquid sensing material was then deposited to surround the tip end of the deflectable arm of the microcantilever and allowed to dry for 24 hours.

FIG. 4 shows the plot from an embedded microcantilever bio-sensor designed to detect the presences of a vaccinia virus in a sample. In this exemplary embodiment, the deflectable arm was embedded within a sensing material comprising a polyclonal vaccinia antibody incorporated into a PEO matrix. The loading of the antibody into the PEO polymer was approximately 50%. A second embedded microcantilever was then constructed in an identical fashion except that the sensing material was pure PEO polymer with not polyclonal vaccinia antibody incorporated therein. A series of experiments with exposing the sensors to aerosols of water vapor and water vapor plus virus were then performed and the results. In the plot shown in FIG. 4, the response of the PEO plus polyclonal vaccinia antibody sensor to the vaccinia virus aerosol minus the same sensor response to water aerosol is plotted. This procedure effectively subtracts the large water vapor response, leaving only the response of the sensor to the analyte virus in the aerosol. In this plot the exposures begin at time (t=100 sec.) and end at time (t=400 sec). After the aerosol exposures end, the sensors were immediately exposed to a flow of dry nitrogen. As can be seen in FIG. 4, some decrease in the maximum peak height occurs upon nitrogen exposure, but the permanent incorporation of virions into the composite matrix of the sensing material prevent the sensor from recovering fully to its original resistance.

Figure 5:
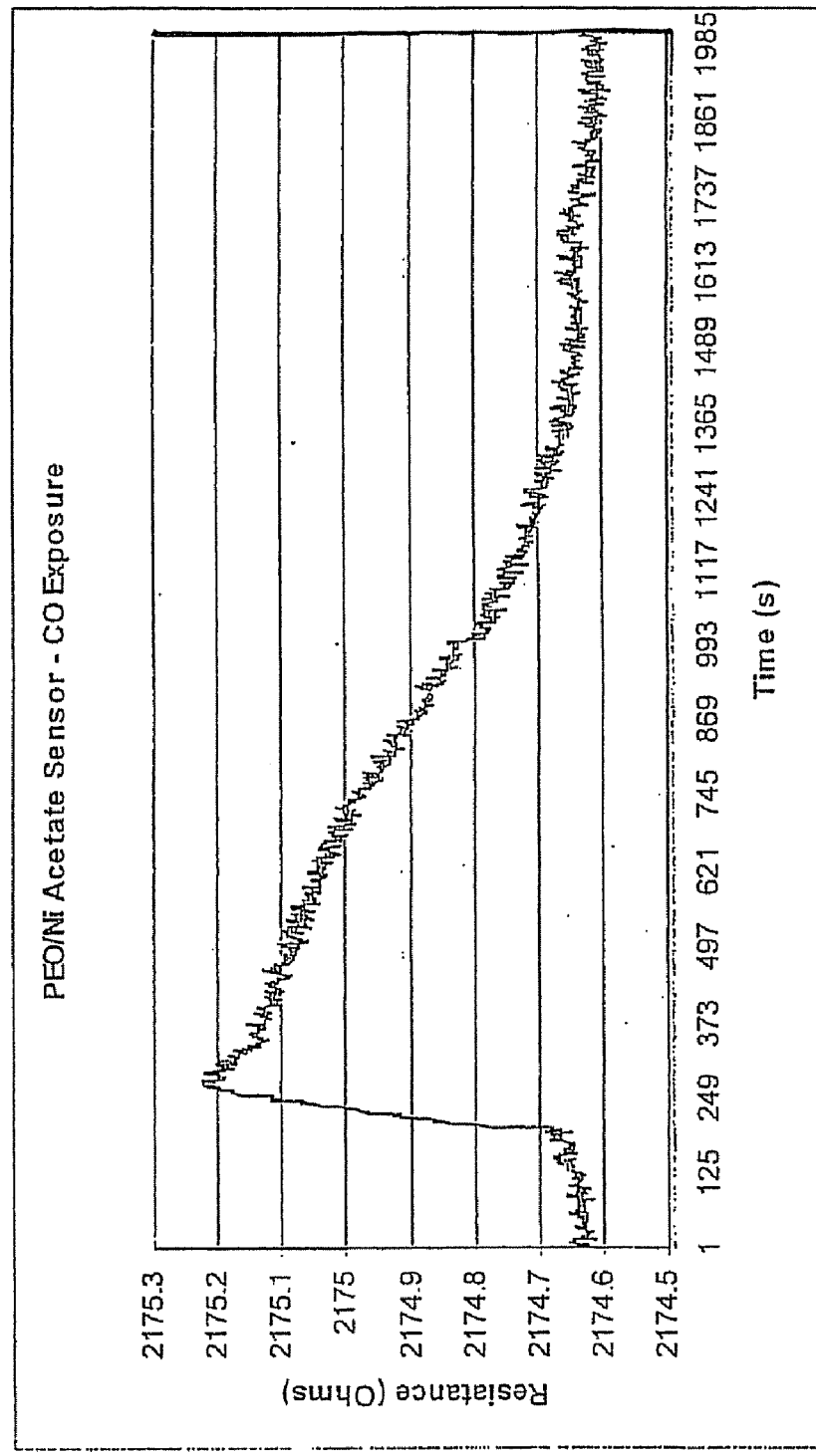
FIG. 5 is a graphical depiction of the response properties of an exemplary embodiment of an embedded microcantilever sensor according to the present invention.

FIG. 5 shows the plot from an embedded microcantilever chemical sensor designed to detect the presence of carbon monoxide (CO) in a sample. In this exemplary embodiment, the deflectable arm was embedded within a sensing material comprising nickel acetate incorporated into a PEO matrix. In the plot shown in FIG. 5, the response of the PEO plus nickel acetate sensor to a 20-second exposure of CO is plotted. In this plot the exposures begin at time (t=250 sec.) and end at time (t=270 sec). As shown, the sensor response is immediate, and after the CO exposures end the sensor slowly recovers to its original resistance.

Figure 6:
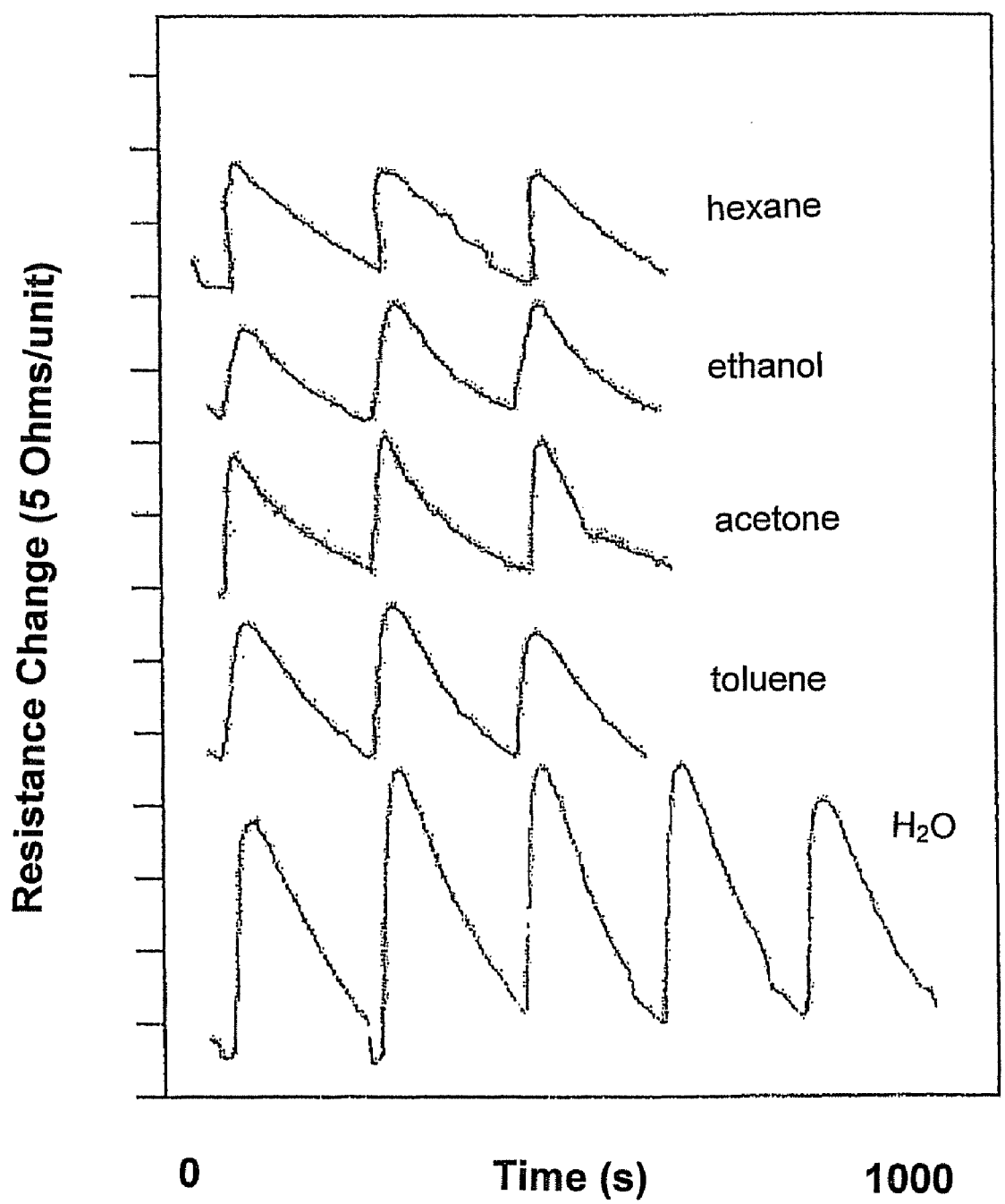
FIG. 6 is a graphical depiction of the response properties of an exemplary embodiment of an embedded microcantilever sensor according to the present invention.

FIG. 6 shows the plot from an embedded microcantilever chemical sensor designed to detect the presence of a variety of volatile organic compounds in a sample. In this exemplary embodiment, the deflectable arm was embedded within a sensing material comprising a lithium perchlorate dopant incorporated into a PEO matrix. In the plot shown in FIG. 6, the responses of the PEO plus lithium perchlorate sensor to an exposure of one of hexane, ethanol, acetone, toluene, and water vapor are plotted. In this experiment all the gases were set at a 50% saturation level with respect to dry nitrogen. Prior to testing the sensor was subjected to four hours of dry nitrogen flow, and the sensor output after this initial period indicated all changes owing to loss of water molecules had been reduced by approximately 97%. In this plot of analyte measurements five cycles of 15 second exposures followed by a 185 second recovery period are plotted. During the recovery period only dry nitrogen was passed over the sensor. As shown, the sensor response is immediate to all five of the analytes with responses in order from smallest to greatest being hexane, ethanol, acetone, toluene, and then water vapor. For all five plots after the initial analyte exposure the sensor slowly recovers to its original resistance.

Because of the large response the PEO sensor shows for water vapor in a preferred embodiment the water vapor signal would be decoupled from that of the other analytes. This decoupling could be accomplished through a number of conventional techniques. In one embodiment, pattern recognition techniques could be used for each analyte with known patterns stored in a memory for comparison for a variety of humidity levels. Alternatively, other polymers with little or not response to water vapor, such as PIB could be used to eliminate or accommodate any large water vapor contaminants.

Much of the behavior of the PEO sensor measurements shown in FIG. 6 to a given analyte may be explained in terms of solubility parameters of the polymer and the analyte vapors. The solubility parameter of PEO is 22.7 MPa.sup.1/2, A table of solubility parameters for the analytes used in this set of experiments is shown in Table 1 below. TABLE-US-00001 TABLE 1 Solubility Parameters H.sub.20 Vapor Hexane Toluene Ethanol Acetone Solubility 48.0 16.7 18.2 26 20.5 Parameter (MPa.sup.1/2)

In general, for the partitioning of organic molecules into an organic host, we expect the greatest degree of partitioning to occur when the organic analyte solubility parameter most closely matches the host solubility parameter. Excluding water vapor, this pattern is followed in the current experiments with the exception of toluene. However, because the sensor response is measured in terms of polymer expansion, the sensor signal will be dependent on the chemical bonding or activity of the analyte molecules with the polymer matrix or dopant. Also the volume expansion may depend on the number of analyte molecules accommodated. Accordingly, once calibration measurements are taken it should be possible to obtain very sensitive qualitative and quantitative information about the analytes in a particular sample.

COMPARATIVE EXAMPLE 1

Although the above examples, provide embodiments of the sensitivity of the sensors according to the present invention, the sensors of the invention are also designed to be rugged when compared to non-embedded microcantilever sensors. As a comparison, in one exemplary embodiment a film approximately 10 micron think of polyvinyl acetate homopolymer, MW 90,000 (Polysciences) was deposited on a glass slide by solvent dip coating the slide in ethyl acetate. The coated slide was then allowed to air dry for 8 hours. A piezoresistive microcantilever (Veeco) was brought into contact with the film and bonded to the glass slide using an epoxy adhesive and a tapered glass shim to appropriately position the cantilever relative to the polymer. The resistance of the cantilever construction was approximately 2,142 ohms. The cantilever sensor was then warmed to 50 C. for 1 hour and cooled to room temperature. The cantilever resistance was then measured to be 2,124 ohms and inspection in a SEM showed that the cantilever was no longer in contact with the polymer, perhaps because additional solvent was removed upon the heating. The sensor was then exposed to 100 PPM of butyl acetate at 25 C. and the resistance monitored. The sensor showed a lag of 3 minutes followed by an increase in resistance. The lag is thought to be due to the time it took the polymer to swell sufficiently to contact the cantilever. It should be noted that the above sensor would not be capable of responding to a contraction of the polymer since it is not mechanically coupled to the polymer.

Example 1

An embedded sensor was made using the same polymer and type of cantilever as described in Comparative Example 1, except that the cantilever was encapsulated with a thin layer of the polymer, again by solvent dipping after being affixed just to contact an approximately 10 micron film of the polymer. This sensor was then elevated to 50 C. for a period of 24 hours and on inspection was determined to still be encapsulated. Upon exposure to 100 PPM of butyl acetate vapor the sensor responded within 5 seconds indicating it was immediately coupled. Because this sensor is embedded within the polymer film it would also be able to respond to a contraction of the polymer caused by cooling or chemical interaction.

COMPARATIVE EXAMPLE 2

A simple stress test was conducted on a sensor constructed as described in Comparative Example 1. In this test a piece of transparent tape was carefully placed atop the cantilever and immediately removed. The cantilever broke and the sensor was rendered inoperative.

Example 2

A simple stress test was then conducted on a sensor constructed as described in Example 1. In this test a piece of transparent tape was carefully placed atop the cantilever and immediately removed. The cantilever was then inspected and found to be intact and operative.

It is emphasized at this point that the present invention is not intended to be limited to the exemplary embodiments shown and described above. Rather, the present invention is intended to cover the method and apparatus which includes the use of an embedded microcantilever having a measurable physical property which changes when the embedded portion of the microcantilever is vertically displaced by a surrounding sensing material which volumetrically changes to deflect the embedded portion of the microcantilever in the presence of a particular analyte or analytes sought to be detected.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A microcantilever sensor, comprising:
a first substrate having an edge;
a polymeric sensing material disposed on a surface of a substrate, said polymeric sensing material capable of a volumetric change when brought into contact with an analyte;
a deflectable arm formed integrally with the first substrate, said arm having a first end fixedly coupled to the first substrate, a second end at least partially embedded in said polymeric sensing material and capable of deflecting responsive to a volumetric change of the polymeric sensing material, and an overhang portion extending beyond the substrate edge; and
a detecting element which creates a detectable signal in response to the deflection of said arm.

2. The microcantilever sensor as in claim 1, wherein said arm includes at least one measurable physical property which changes when said arm deflects and said detecting element is capable of measuring a change in said at least one measurable physical property at least one point along said arm.

3. The microcantilever sensor as in claim 2, wherein said detecting element is capable of measuring a change in said at least one measurable physical property at a plurality of locations along said arm.

4. The microcantilever sensor as in claim 1, in which said detecting element includes an electric circuit for facilitating measurement of said deflection of said arm.

5. The microcantilever sensor as in claim 1, in which said detecting element includes a transducer capable of transducing said deflection of said arm to a measurable electrical signal.

6. The microcantilever sensor as in claim 1, in which said deflectable arm includes a piezoresistive member formed one of therein or thereon and said detecting element includes an electrical circuit capable of measuring a change in resistance of said piezoresistive member due to said deflection.

7. The microcantilever sensor as in claim 5, wherein said piezoresistive member comprises barium titanate.

8. The microcantilever sensor as in claim 1, wherein said polymeric sensing material comprises at least one material selected from the group consisting of polyvinyl acetate (PVA), polylsobutylene (PIB), polyethylene vinyl acetate (PEVA), poly(4-vinylphenol), poly(styrene-co-allyl alcohol), poly(methylstyrene), poly(N-vinylpyrrolidone), poly(styrene), poly(sulfone), poly(methyl methacrylate), and poly(ethylene oxide).

9. A method for detecting an analyte within a medium, comprising:
providing a microcantilever sensor according to claim 1;
measuring a control volume of said polymeric sensing material by monitoring the deflection of said deflectable arm in the absence of said analyte;
introducing a medium containing said analyte to said microcantilever sensor, said medium being one of a liquid and a vapor; and
comparing the control volume to a measured volume in the presence of said medium by monitoring said deflection of said microcantilever arm.

10. The method as in claim 9, wherein said deflectable arm includes at least one measurable physical property which changes when said deflectable arm deflects and said measuring comprises measuring a change in said at least one measurable physical property.

11. The method as in claim 9, wherein said deflectable arm includes a piezoresistive member one of therein and thereon, and said measuring comprises measuring a resistance change of said piezoresistive member as a result of one of said upward deflection and said downward deflection.

12. The method as in claim 11, in which said deflectable arm includes two conductive leads coupled to said piezoresistive member and said measuring includes measuring resistance across said two conductive leads.

* * * * *